United States Patent
Vale et al.

(10) Patent No.: US 10,588,561 B1
(45) Date of Patent: Mar. 17, 2020

(54) NONINVASIVE SYSTEM AND METHOD FOR MAPPING EPILEPTIC NETWORKS AND SURGICAL PLANNING

(71) Applicants: Fernando Vale, Tampe, FL (US); Elliot George Neal, Tampa, FL (US)

(72) Inventors: Fernando Vale, Tampe, FL (US); Elliot George Neal, Tampa, FL (US)

(73) Assignee: University of South Florida, Tampa, FL (US)

( * ) Notice: Subject to any disclaimer, the term of this patent is extended or adjusted under 35 U.S.C. 154(b) by 88 days.

(21) Appl. No.: 16/024,020

(22) Filed: Jun. 29, 2018

Related U.S. Application Data

(60) Provisional application No. 62/549,604, filed on Aug. 24, 2017.

(51) Int. Cl.
  *A61B 5/00*  (2006.01)
  *G01R 33/563*  (2006.01)
  (Continued)

(52) U.S. Cl.
  CPC .......... *A61B 5/4094* (2013.01); *A61B 5/0042* (2013.01); *A61B 5/04014* (2013.01); *A61B 5/0476* (2013.01); *G01R 33/4806* (2013.01); *G01R 33/4808* (2013.01); *G01R 33/56341* (2013.01); *A61B 5/0035* (2013.01); *A61B 5/055* (2013.01); *A61B 5/4064* (2013.01);
  (Continued)

(58) Field of Classification Search
  CPC . A61B 5/4095; A61B 5/0042; A61B 5/04014; A61B 5/0476; G01R 33/4806; G01R 33/4808; G01R 33/56341
  See application file for complete search history.

(56) References Cited

U.S. PATENT DOCUMENTS

2003/0050527 A1\* 3/2003 Fox .................... A61N 2/02
  600/13
2006/0241382 A1\* 10/2006 Li .................... A61B 5/055
  600/410

(Continued)

OTHER PUBLICATIONS

Ottenhausen, Krieg, Meyer, and Ringel, "Functional preoperative and intraoperative mapping and monitoring: increasing safety and efficacy in glioma surgery", Neurosurg Focus, 38, 1-13 (Year: 2015).\*

(Continued)

*Primary Examiner* — Joanne M Hoffman
(74) *Attorney, Agent, or Firm* — Molly L. Sauter; Smith & Hopen, P.A.

(57) ABSTRACT

System and method for processing, non-concurrently collected, electroencephalogram (EEG) data and resting station functional magnetic resonance imaging (rsfMRI) data, non-invasively, to create a patient-specific three-dimensional (3D) mapping of the patient's functional brain network. The mapping can be used to more precisely identify candidates of resective neurosurgery and to help create a targeted surgical plan for those patients. The methodology automatically maps the patient's unique brain network using non-concurrent EEG and resting state functional MRI (rsfMRI). Generally, the current invention merges non-concurrent EEG data and rsfMRI data to map the patient's epilepsy/seizure network.

17 Claims, 14 Drawing Sheets
(11 of 14 Drawing Sheet(s) Filed in Color)

(51) Int. Cl.
  *A61B 5/04* (2006.01)
  *G01R 33/48* (2006.01)
  *A61B 5/0476* (2006.01)
  *G01R 33/56* (2006.01)
  *A61B 5/055* (2006.01)

(52) U.S. Cl.
  CPC .......... *A61B 5/7235* (2013.01); *A61B 5/7285* (2013.01); *G01R 33/5608* (2013.01); *G06T 2207/10088* (2013.01); *G06T 2207/30016* (2013.01)

(56) References Cited

U.S. PATENT DOCUMENTS

| | | | | |
|---|---|---|---|---|
| 2011/0190621 | A1* | 8/2011 | Verdoorn | G06K 9/0057 600/411 |
| 2012/0296569 | A1* | 11/2012 | Shahaf | A61B 5/048 702/19 |
| 2013/0096408 | A1* | 4/2013 | He | A61B 5/04008 600/378 |
| 2013/0113816 | A1* | 5/2013 | Sudarsky | G06T 11/206 345/589 |
| 2013/0123607 | A1* | 5/2013 | Leuthardt | A61B 5/0042 600/410 |
| 2013/0131438 | A1* | 5/2013 | Brewer | A61M 21/02 600/28 |
| 2013/0267827 | A1* | 10/2013 | Grodzki | A61B 5/0042 600/411 |
| 2014/0180060 | A1* | 6/2014 | Parrish | G01R 33/4806 600/411 |
| 2014/0343399 | A1* | 11/2014 | Posse | A61B 5/055 600/410 |
| 2015/0164431 | A1* | 6/2015 | Terry | A61B 5/4094 600/408 |
| 2017/0238879 | A1* | 8/2017 | Ducreux | A61B 5/7264 |
| 2018/0199848 | A1* | 7/2018 | Wendling | A61B 5/04842 |

OTHER PUBLICATIONS

Olbrich, Mulert, Karch, Trenner, Leicht, Pogarell, Hegerl, "EEG-vigilance and BOLD effect during simultaneous EEG/fMRI measurement", NeuroImage, 45, 319-332 (Year: 2009).*

Tyvaert, Hawco, Kobayashi, LeVan, Dubeau, Gotman, "Different structures involved during ictal and interictal epileptic activity in malformations of cortical development: an EEG-fMRI study", Barin, 131, 1-32 (Year: 2013).*

* cited by examiner

```
                    ┌─────────────────────────────────────────┐
                    │ Generating a 3D Mapping of the Patient's│
                    │              Brain Network              │
                    │                  405                    │
                    └────────────────────┬────────────────────┘
                                         ▼
                    ┌─────────────────────────────────────────┐
                    │ Importing A Diffusion Tensor MRI (DT-MRI)│
                    │      Volume into Tractography           │
                    │             Pre-Processor               │
                    │                  410                    │
                    └────────────────────┬────────────────────┘
                                         ▼
                    ┌─────────────────────────────────────────┐
                    │ Interpolating the DT-MRI Data and       │
                    │ Calculating a Diffusion Tensor for Each │
                    │       Voxel of the DTI-MRI Data         │
                    │                  415                    │
                    └────────────────────┬────────────────────┘
                                         ▼
                    ┌─────────────────────────────────────────┐
                    │ Calculating All Fibers Above a          │
                    │ Predetermined Fractional Anisotropy     │
                    │               Threshold                 │
                    │                  420                    │
                    └────────────────────┬────────────────────┘
                                         ▼
                    ┌─────────────────────────────────────────┐
                    │ Display Fibers that Cross Through       │
                    │ Selected ROIs to Visual the Interictal  │
                    │            Seizure Network              │
                    │                  425                    │
                    └─────────────────────────────────────────┘
```

FIG. 4

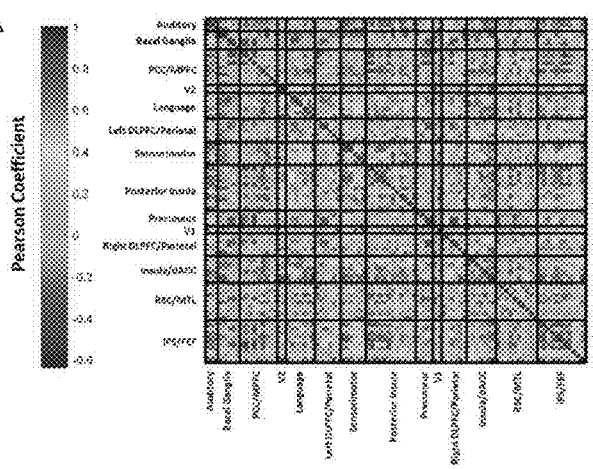
FIG. 7A
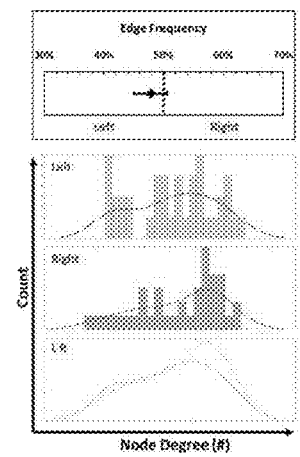
FIG. 7B
FIG. 7C

FIG. 8A
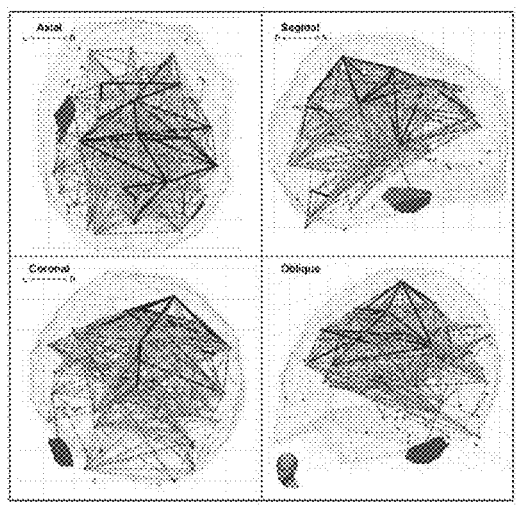
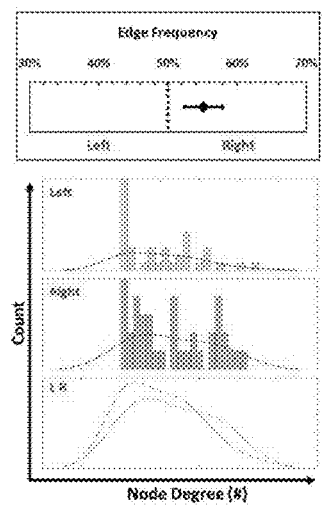
FIG. 8B
FIG. 8C

NONINVASIVE SYSTEM AND METHOD FOR MAPPING EPILEPTIC NETWORKS AND SURGICAL PLANNING

CROSS-REFERENCE TO RELATED APPLICATIONS

This application claims priority to U.S. Provisional Application No. 62/549,604, filed on Aug. 24, 2017, and entitled "PATIENT-SPECIFIC EPILEPSY NETWORK MODELING".

FEDERALLY SPONSORED RESEARCH OR DEVELOPMENT

This invention was made with Government support under 2017 Neurosurgery Research and Education Foundation (NREF) Medical Student Summer Research Fellowship. The government has certain rights in the invention.

BACKGROUND OF THE INVENTION

1. Field of the Invention

This invention relates, generally, to brain mapping. More specifically, it relates to epilepsy networking modeling and simulation of planned surgery.

2. Brief Description of the Prior Art

Epilepsy is one of the most common neurologic disorders, with prevalence of 0.5%-1%. Current data show that epilepsy in 20%-30% of patients is refractory to medical therapy and these patients are therefore possible candidates for resective neurosurgery.

Surgical candidates are evaluated using magnetic resonance imaging (MRI) to evaluate brain structure and electroencephalograph), (EEG) to identify and localize ictal and interictal activity. These two techniques are the most common ways to identify epileptic foci for targeted resection. Wada testing, functional MRI (fMRI) and neuropsychological evaluation are used to determine laterality of speech and memory function to minimize morbidity. Despite rigorous pre-surgical evaluation, resective surgery achieves seizure freedom in only two-thirds of cases, so one-third of patients still suffer from seizures post-surgery. Increasing the effectiveness of surgery will most likely either come from more accurate and precise surgical target mapping or more specific identification of candidates who will be responsive to surgery.

Epilepsy has recently been reimagined as a network-level disorder, which may explain why many patients fail focal resection. Alteration of global brain networks, mapped using graph theory techniques, has been shown in patients with epilepsy. Network-level alterations are characterized by decreased connectivity globally, decreased connection to the default-mode network and increased small-world network segregation in the region of epileptogenic tissue. Recent studies have demonstrated the value of resting state functional MRI (rsfMRI) in mapping brain networks. The epileptogenic cortex can be identified by applying EEG, source localization algorithms.

Despite recent improvements in technology, no generally available method is capable of mapping the network-level disturbances resulting from epileptic discharges using conventional hardware, which includes MRI and scalp EEG. More specifically, evidence shows that network-level disturbances resulting from epileptic discharges may explain why some patients do not respond to surgery. However, current assessments do not evaluate the individual network architecture and no tool exists that automatically maps each patient's brain network. As such, current preoperative evaluation does not include a detailed network analysis despite the association of network-level changes with epilepsy.

Accordingly, what is needed is a system and method for mapping individualized epilepsy networks. Furthermore, a software algorithm is needed that can be used to plan surgeries that most effectively disconnect the mapped network. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

In various embodiments, the present invention provides a system and method for mapping individualized epilepsy networks of patients and simulating planned resective surgeries by combining non-invasive electroencephalography (EEG) source localization and nonconcurrent resting state functional magnetic resonance imaging (rsfMRI).

In one embodiment, the present invention provides a method for generating a functional brain map of a patient. The method includes, providing electroencephalogram (EEG) data acquired non-invasively from a patient, providing resting state functional magnetic resonance imaging (rsfMRI) data acquired non-invasively from the patient, wherein the EEG data and the rsfMRI data were acquired from the patient non-concurrently and co-registering the EEG data and the rsfMRI data of the patient to generate a functional brain map of the patient.

Co-registering the EEG data and the rsfMRI data of the patient to generate a functional brain map of the patient further may further include, cropping the EEG data to provide representative ictal waveforms and interictal waveforms, band-pass filtering the EEG data to remove nonphysiologic signals from the EEG data, notch filtering the band-pass filtered EEG data to remove background electronic noise from the EEG data, inversely solving the cropped, band-pass filtered and notch filtered EEG data to generate 3D spatial coordinates that localize source of cortical discharges and exporting the 3D spatial coordinates from the EEG data as a 3D volume. The method may further include, overlaying the 3D volume of a 3D mesh model from the rsfMRI data.

The EEG data comprises ictal and interictal events and the rsfMRI data comprises a set of time-series rsfMRI data. As such, co-registering the EEG data and the rsfMRI data of the patient to generate a function brain map of the patient may further includes, defining regions of interest (ROIs) for each ictal and interictal event, extracting median time series data from the rsfMRI data for each ictal and interictal event ROI, comparing the median time series for each ictal and interictal event ROI to each rsfMRI voxel time series to determine a correlation value for the voxel and exporting 3D volumes of the voxels having correlation values exceeding a predetermined threshold. The method further includes defining functional regions of interest (ROIs) from the rsfMRI data, calculating and extracting median MRI time series data, scaled to the mean, for each ROI, comparing the time series data for each ROI to every other ROI time series data to calculate a correlation coefficient for each ROI-to-ROI connection to generate correlation scalars and constructing a 3D graph with mapped vectors representing pairs of correlating ROI's based on the correlation scalars.

In another embodiment, the present invention provides a system for non-invasively generating a functional brain map of a patient, which includes, an input for receiving electroencephalogram (EEG) data acquired non-invasively from a patient and resting state functional magnetic resonance imaging (rsfMRI) data acquired non-invasively from the patient, wherein the EEG data and the rsfMRI data were acquired from the patient non-concurrently and at least one processor and associated software for co-registering the EEG data and the rsfMRI data of the patient to generate a functional brain map of the patient.

In another embodiment, the present invention provides, a non-transitory computer readable storage media having computer-executable instructions, having computer-executable instructions for performing a method of running a software program on a computing device for the generation of a functional brain map of a patient, the computing device operating under an operating system, the method including issuing instructions from the software program including, providing electroencephalogram (EEG) data acquired non-invasively from a patient, providing resting state functional magnetic resonance imaging (rsfMRI) data acquired non-invasively from the patient, wherein the EEG data and the rsfMRI data were acquired from the patient non-concurrently and co-registering the EEG data and the rsfMRI data of the patient to generate a functional brain map of the patient.

Once the functional map has been generated, the user is able to trace a predicted surgical resection volume model. This volumetric tracing is then used to subtract the functionally connected components of the map that intersect with the tracing of the predicted surgery. Then, the subtracted map is compared to the original map, and used to assess the predicted degree of disconnection. In this way, it may be possible to predict which type of surgery will be likely to disconnect the network and therefore effectively treat the epilepsy.

Accordingly, in various embodiments, the present invention provides a system and method for the determination of a functional mapping of a patient's brain and modelling of predicted surgery which utilizes non-invasive EEG and rsfMRI data that has been collected non-concurrently.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 4 is a flowchart depicting a step-by-step methodology of visualizing a seizure network from a 3D head model of a patient, according to an embodiment of the current invention.

FIG. 7A illustrates a statistical analysis of the global resting network in a healthy control patient, including a correlation matrix between ninety pre-defined functional ROIs with functional grouping labeled on the X and Y axis. Pearson correlation coefficients were color-coded, with the color legend adjacent.

FIG. 7B illustrates frequency of edges with above-mean Pearson coefficients. Edges are symmetrically distributed between left and right hemispheres with 99 T confidence interval (Wald method).

FIG. 7C illustrates the nodal degree of connectivity determined by the number of intersecting edges with a Pearson coefficient above the global mean. Nodal degree represents a measurement of network integration, which is plotted as a histogram for both left and right hemispheres. Connections were symmetrically distributed between left (41.2±16.7) and right (43.7±16.7) hemispheres.

FIG. 8A illustrates focal left temporal lobe epilepsy, where the global resting network is shown in a 3D map. The model shows connections distributed asymmetrically, with a relative paucity of connections ipsilateral to the epileptogenic brain region.

FIG. 8B illustrates the frequency of edges with above-mean Pearson coefficients is relatively lower ipsilateral to the epileptogenic tissue (99% confidence interval).

FIG. 8C illustrates nodes located in the right hemisphere have significantly (p b 0.01) higher degree of connectivity (44.7±16.4 connections) compared with the left hemisphere (37.3±20.5 connections).

DETAILED DESCRIPTION OF THE PREFERRED EMBODIMENT

Figure 1:
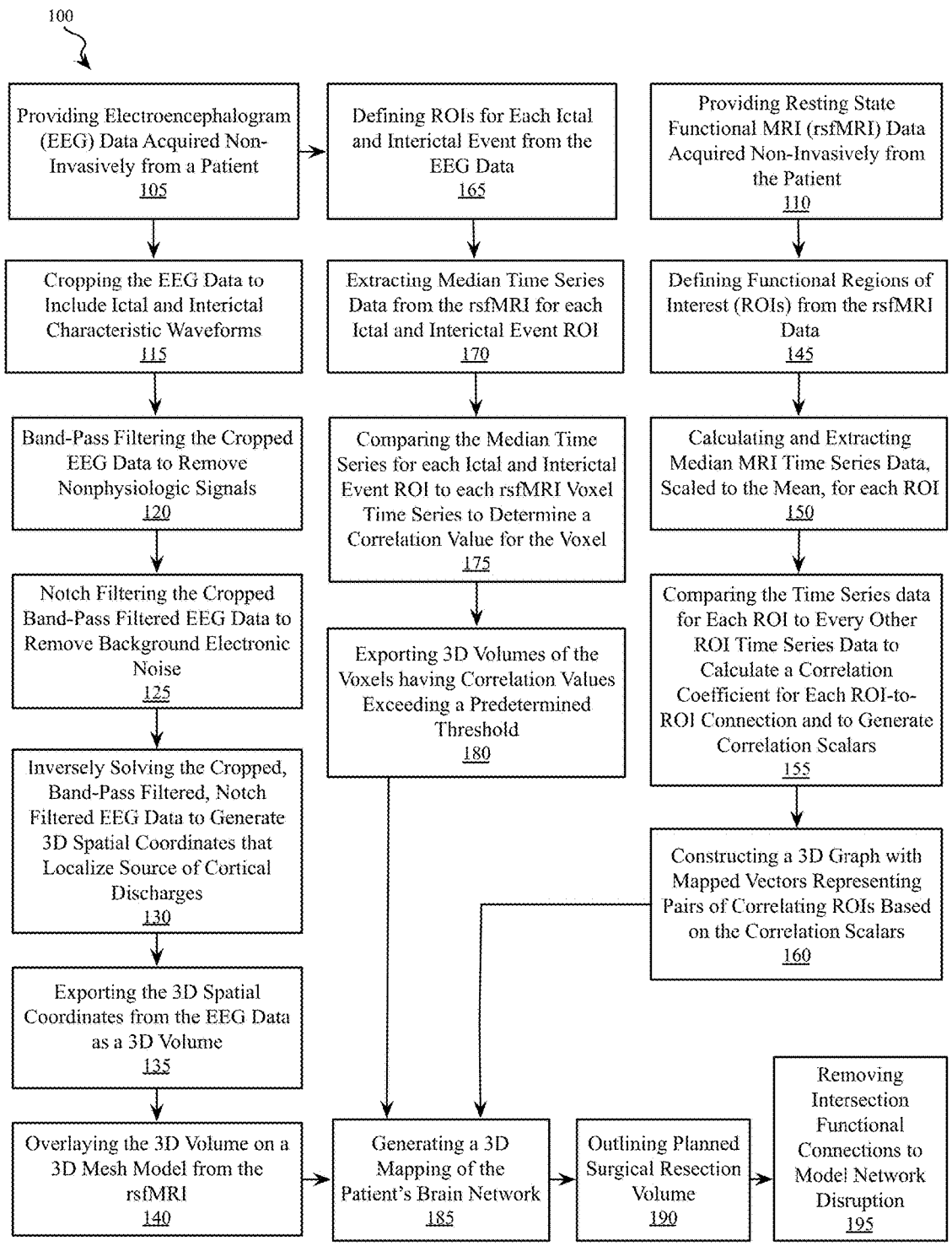
FIG. 1 is a flowchart depicting a step-by-step methodology of generating a 3D head model of a patient, according to an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The field of individualized network analysis is still in its infancy and potential uses of this technology can be categorized into three broad categories: diagnosis of epilepsy, identification of surgical candidates and localization of surgical resection targets. Supporting evidence for the first category includes studies showing connectivity parameters from rsfMRI and EEG synchronicity used to create "biomarkers" for diagnosis of epilepsy and measure the progression of the seizure-related atrophy. For the second category, network asynchrony local to the epileptogenic focus and network correlation similarities with the retrospective cohort of patients with Engel class III-IV outcomes post-surgery, have been used to prospectively identify ideal candidates who will have the best outcomes after surgery. Finally, surgical targeting and resection of functional hubs, or network relay points, have been correlated with better surgical outcomes.

In accordance with various embodiments of the present invention, scalp EEG data and rsfMRI data are acquired from a patient, non-concurrently. Data from the rsfMRI is then preprocessed and a time-series function is extracted. Connection coefficients are then used to threshold out spurious connections and to thereby model global functional networks in a 3D map. Epileptic discharges were from the EEG data are localized using a forward model or cortical mesh dipoles followed by an empirical Bayesian approach of inverse source reconstruction, which are then co-registered with the rsfMRI time series function, thereby mapping co-activating brain regions.

Network mapping is made possible by taking measurements of brain activity over time and interpreting the data using a combination of correlation analysis, causality analysis and graph-theory mapping techniques that implement correlation and/or causation to create a directed or non-directed graph. Noninvasive scalp EEG is a sensitive modality to detect epileptiform discharges and has unmatched temporal resolution. However, it is characteristically limited in spatial accuracy because of the dampening effects of the brain, cerebrospinal fluid (CSF), bone and skin. Comparatively, rsfMRI has better spatial resolution buts lacks the temporal resolution needed to localize propagation patterns of ictal or interictal discharges. The present invention overcomes the deficiencies in these two techniques of network mapping, by combining the two datasets to maximize the benefits and minimize the drawbacks of both technologies. While concurrently measured EEG and rsfMRI have been used to map brain connectivity, the specialized hardware required is not commonly available. Stereoencephalography (SEEG) has been used in connectivity studies to dramatically improve the spatial accuracy of EEG measurements. However, SEEG is necessarily an invasive measurement tool and is therefore not appropriate for all patients with epilepsy.

The present invention provides a system and method that co-registers nonconcurrent scalp EEG and rsfMRI data to create a 3D network map of each patient with epilepsy. The data from the scalp EEG and the rsfMRI are acquired nonconcurrently so that the method is optimized for analysis of data collected on commonly available scalp EEG and diagnostic MRI machines. The system and method of the present invention are the first to map the epilepsy network, noninvasively, utilizing nonconcurrent EEG and rsfMRI data.

In various embodiments, the present invention processes electroencephalogram (EEG) data and magnetic resonance imaging (MRI) data noninvasively to create a patient-specific three-dimensional (3D) image that can be used to more precisely identify candidates for resective neurosurgery and to help create a targeted surgical plan for those patients. The methodology maps the patient's unique brain network using nonconcurrent EEG and resting state functional MRI (rsfMRI). Generally, the present invention merges nonconcurrent EEG data and rsfMRI data to map the patient's epilepsy/seizure network. Nonconcurrent data facilitates collection of data from the patient and makes this data more widely available since it does not require the patient to be in the MRI scanner for long periods of time.

With reference to FIG. 1, in certain embodiments, the methodology 100 proceeds as shown. The method includes, providing EEG data acquired non-invasively from a patient 105 and providing rsfMRI data acquired non-invasively from the patient 110. The EEG data is then cropped to include only ictal and interictal characteristic waveforms 110, as defined by a trained neurologist. The cropped EEG data is then band-pass filtered, to remove nonphysiologic signals 115. In one embodiment, the cropped EEG is band-pass filtered between 0.1 and 100 hertz. The cropped EEG band-pass filtered data is subsequently notch filtered to remove background electronic noise 120. In one embodiment the cropped EEG band-pass filtered data is notch filtered between 59 and 61 Hz. The cropped, band-pass filtered and notch filtered EEG data is then co-registered with a unique patient-specific brain model generated using a three-sphere boundary element model 125. Then, the cropped and filtered EEG data then inversely solved to generate 3D spatial coordinates that localize the source of cortical discharges 130. The 3D spatial localization coordinates from the EEG data are then exported as a 3D volume 135. The 3D volume is then overlayed on a 3D mesh model obtained from the patient's rsfMRI 140.

Processing the rsfMRI data includes, defining functional regions of interest (ROIs) on the rsfMRI image set as distinct areas of the brain that are cooperative in function 145. The method further includes, calculating and extracting median MRI time series data, scaled to the mean, for each ROI 150. The method continues by comparing the time series data for each ROI to every other ROI time series data to calculate a correlation coefficient for each ROI-to-ROI connection and to generate correlation scalars 155. The correlation scalars are used to quantify strength of connections between ROIs in a resting state. These correlation scalars are then used to construct a 3D graph with mapped vectors representing pairs of correlating ROIs 160, as a series of 3D points and vectors.

The EEG source data is then used to generate a second set of ROIs for each ictal and interictal event 165. Median time series data is then extracted from these ictal and interictal event ROIs 170, and an individual component analysis is conducted to compare each ictal and interictal event ROI with every other rsfMRI voxel time series 175. Voxels that exhibit a high enough correlation with the ictal or interictal ROIs are then exported as 3D volumes 180, such as voxels having a correlation value that exceeds a predetermined threshold value.

Resting state connections derived from the rsfMRI data, EEG source localization derived from the EEF data, and ictal/interictal connected voxel data derived from both the rsfMRI data and the EEG data is plotted in reference to a 3D head model, that is automatically generated from the patient's MRI, to generate a 3D mapping of the patient's brain network 185.

The user interface of the underlying software can import, pre-process, map, and plot this data in a user-friendly environment. It is compatible with any scalp EEG system and any MRI scanner. This software would be easily applied at any center interested in evaluating epilepsy patients, with the only necessary equipment being that which is likely already owned by the hospital or clinic.

In an exemplary embodiment, electroencephalography (EEG) data and rsfMRI data are acquired for a patient with epilepsy. EEG acquisition may be performed with scalp electrodes in a standard 10-20, 10-10, or 10-5 configuration. This type of surface EEG is available at most clinics and hospitals with a neurology department. EEG data is exported in European Data Format (EDF) format, a standard open source EEG data file.

rsfMRI may be conducted in a 1.5 T or 3 T MRI capable of brain imaging, with a blood oxygen dependent (BOLD) MRI sequence. A voxel size of 2 mm cubed has been validated, but any voxel size is contemplated herein. rsfMRI is acquired while the patient is lying supine with eyes closed and as still as possible. In addition to a rsfMRI sequence, a volumetric T1-weighted thin slice MRI can also be acquired for maximum spatial accuracy and to identify cortex. This sequence is acquired as part of a standard epilepsy evaluation. A diffusion tensor MRI (DTI-MRI) is also acquired, which includes a series of corresponding gradient echo diffusion images and a B0 image, which is all a standard MRI sequence available on most MRI acquisition software versions. MRI data is exported in a DICOM format, which is the universal medical image file format.

As previously described, in this exemplary embodiment, EEG data was cropped so as to include only ictal and interictal characteristic waveforms, as defined by a neurologist. The EDF file was cropped by removing all data outside of the defined periods of ictal and interictal activity. Next, the EEG data was band-pass filtered between 0.1 and 100 hertz to remove non-physiologic signals using a digital filter in MATLAB) a computer programming software). EEG data was subsequently notch filtered between 59 and 61 hertz to remove background electronic noise, also using MATLAB.

Filtered EEG data was then co-registered with a unique patient-specific brain model generated using a three-sphere boundary element model. The three-sphere boundary model creates three volumes to simulate the signal dampening effects of brain tissue, cerebrospinal fluid, and bone. The three-sphere model was used to approximate an inverse source solution with maximum accuracy. Once a model of the patient's head is created, the ictal and interictal EEG signals are inversely solved to localize the source of cortical discharges. To do this, a source discharge waveform was estimated by averaging the collection of discharges measured at the scalp electrodes that sense the signal. Then, the modeled discharge waveform was simulated at each brain voxel with the effects of physiological dampening. The simulation results in a predicted surface signal at each virtual surface electrode. The modeled surface measurement is compared to the actual measured signal at the matching electrode, and a degree of correlation is calculated.

The simulated discharges that have the highest average correlation across each of the electrodes correspond to the brain voxel that most likely represents the source of the ictal or interictal discharge. The resulting data is a collection of 3D spatial coordinates with a corresponding numeric value representing the likelihood that it was the location of the epileptic discharge. This set of 3D data was exported as a volume. The volume was automatically overlaid on the 3D mesh model created from the patient's MRI. EEG sources are color coded by event number and event type, where solid dots represent interictal discharges and crosses represent ictal discharges.

The rsfMRI data is a collection of 3D volumes that measures the average blood oxygenation at each brain voxel, over time. The rsfMRI is used to create a time-series function for each brain voxel. In this exemplary embodiment, functional regions of interest (ROI) are defined as a set of ninety ROIs that were identified as cooperatively coordinated in the resting brain state. For each ROI, the voxels inside were taken collectively and a median time series data, scaled to the mean for each ROI, was calculated and extracted within MATLAB.

Figure 2:
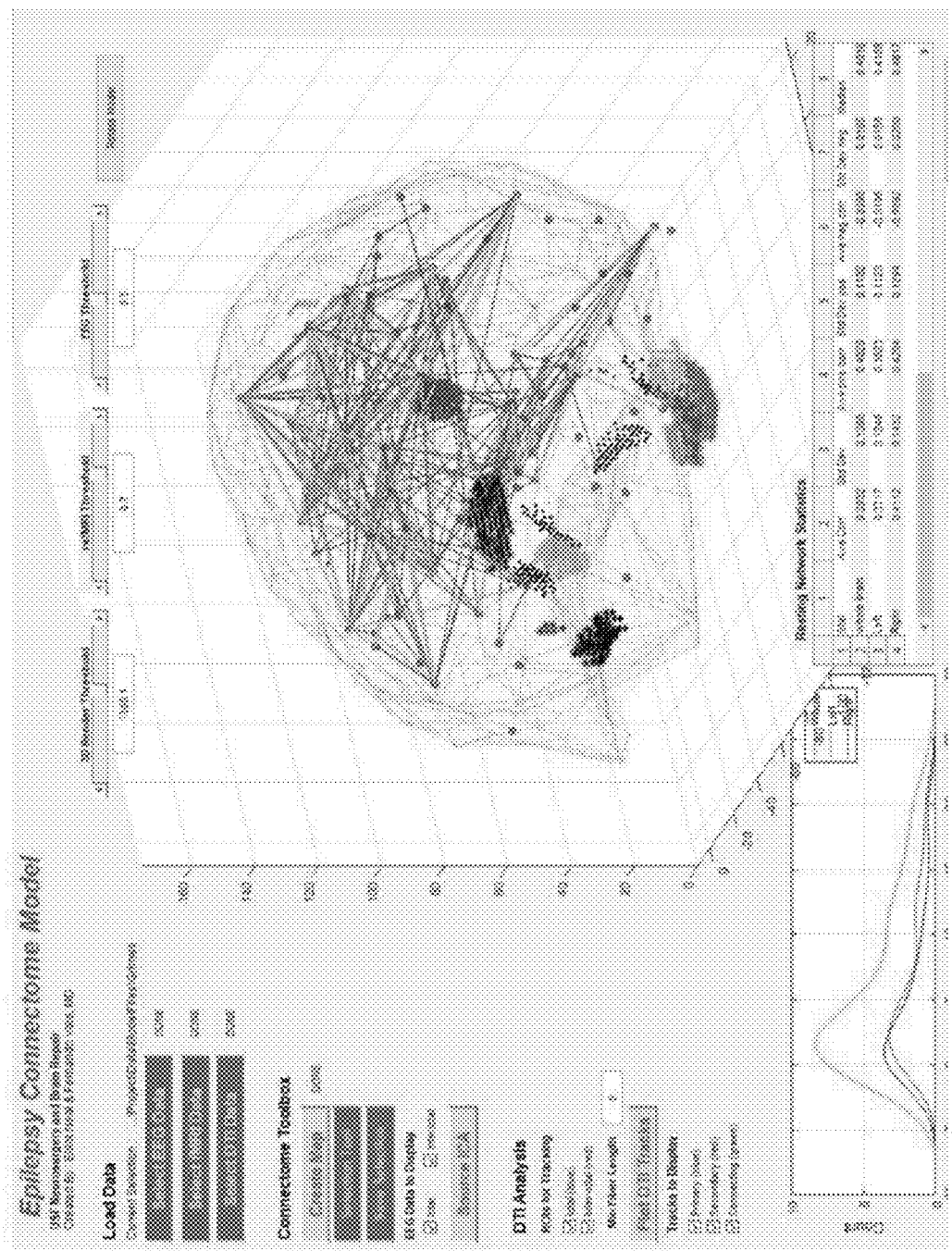
FIG. 2 depicts a 3D mesh (red) constructed to represent a patient's brain. Solid lines represent the resting connections in a color-coded scheme where blue is lowest connectivity and orange is highest. The multicolor dots represent the EEG source localization data. Each color represents a distinct event and dots represent interictal events while crosses represent ictal events. Along the bottom of are representative statistics describing the global resting network.

These representative time series were then compared to each other, generating a Pearson linear correlation coefficient for each ROI-to-ROI connection. This results in a 90 by 90 matrix with scalar values in each cell representing the correlation of each connection between functional ROIs. This connection map was then used to calculate modular connectivity, average connectivity, average degree of connectivity, and asymmetry in both numbers and strength of connections. These values were used to measure the global network in each patient. Finally, the matrix is used to construct a 3D map with lines between ROIs representing a connection above a user-selected threshold, with a color-coding scheme that represents the strength of correlation between the two ROIs. This 3D map is overlaid on the 3D mesh map of the patient's brain, as shown in FIG. 2.

Subsequently, a more targeted approach was taken to measure the network relating specifically to the epileptic region. In this targeted approach, the 3D dataset generated from the EEG source localization is spatially co-registered with the rsfMRI data set by transforming each to a standard MNI coordinate system using MATLAB.

Figure 3:
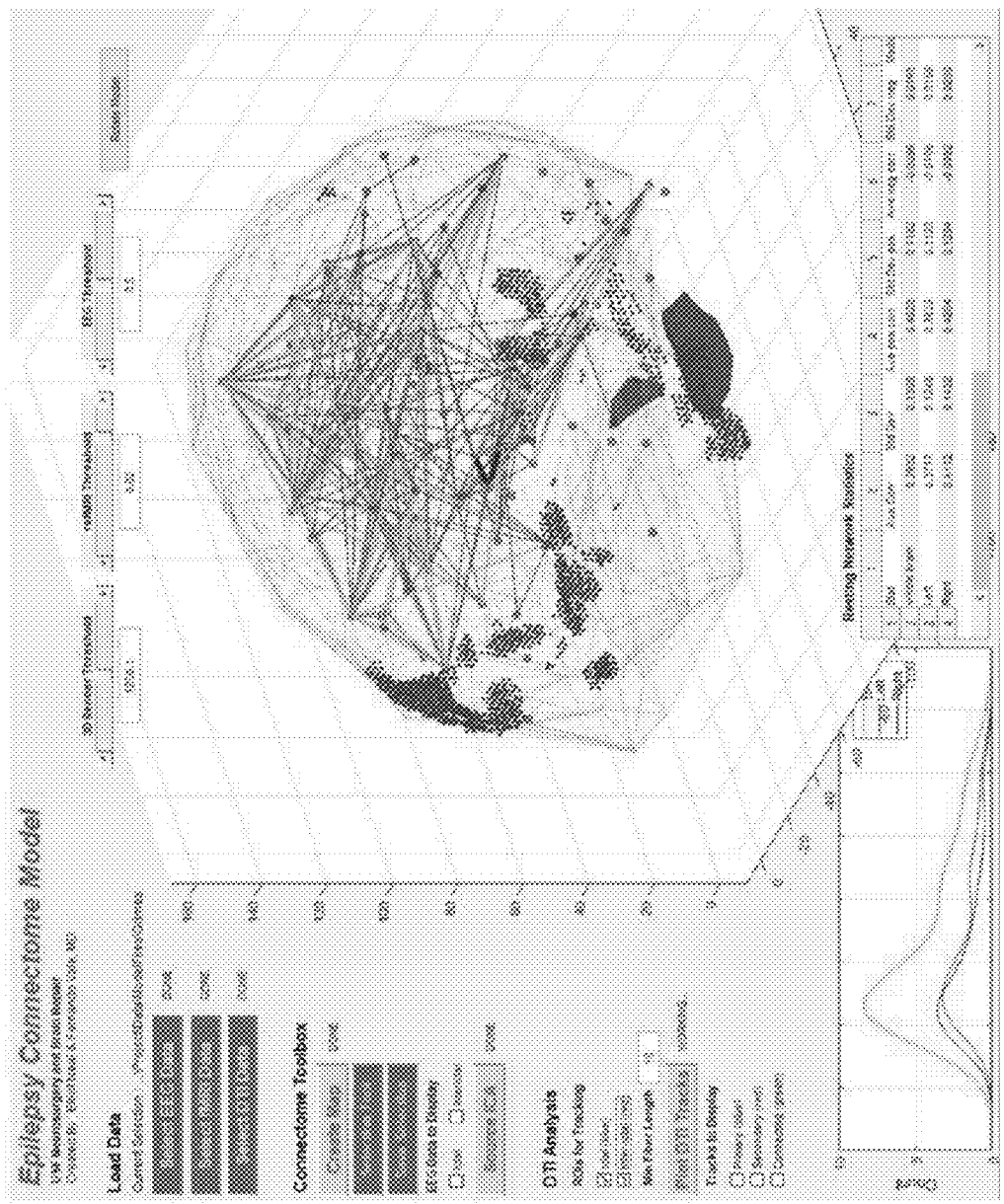
FIG. 3 depicts user-selected ROIs, displayed as red (interictal) and blue (ictal) solid objects. The connecting voxels are represented as dots (red=interictal, and blue=ictal). This map shows both the seizure discharges and the cooperating brain regions as measured using the rsfMRI.

A user may then select which ictal and/or interictal regions to include for analysis by dragging a selection box over the graphical user interface. Once selected, the user-defined ROI may be used to calculate a median rsfMRI time series that is scaled to the mean for the ROI. This time series, representative of the user-defined ROI, is then compared to every voxel in the rsfMRI image set to generate a 3D map of voxels that most correlate with the EEG source. At this point, the user has generated a map of the global resting network connections, the EEG source data, and the mapped voxels that functionally correlate to the EEG source, as shown with reference to FIG. 3.

Figure 5:
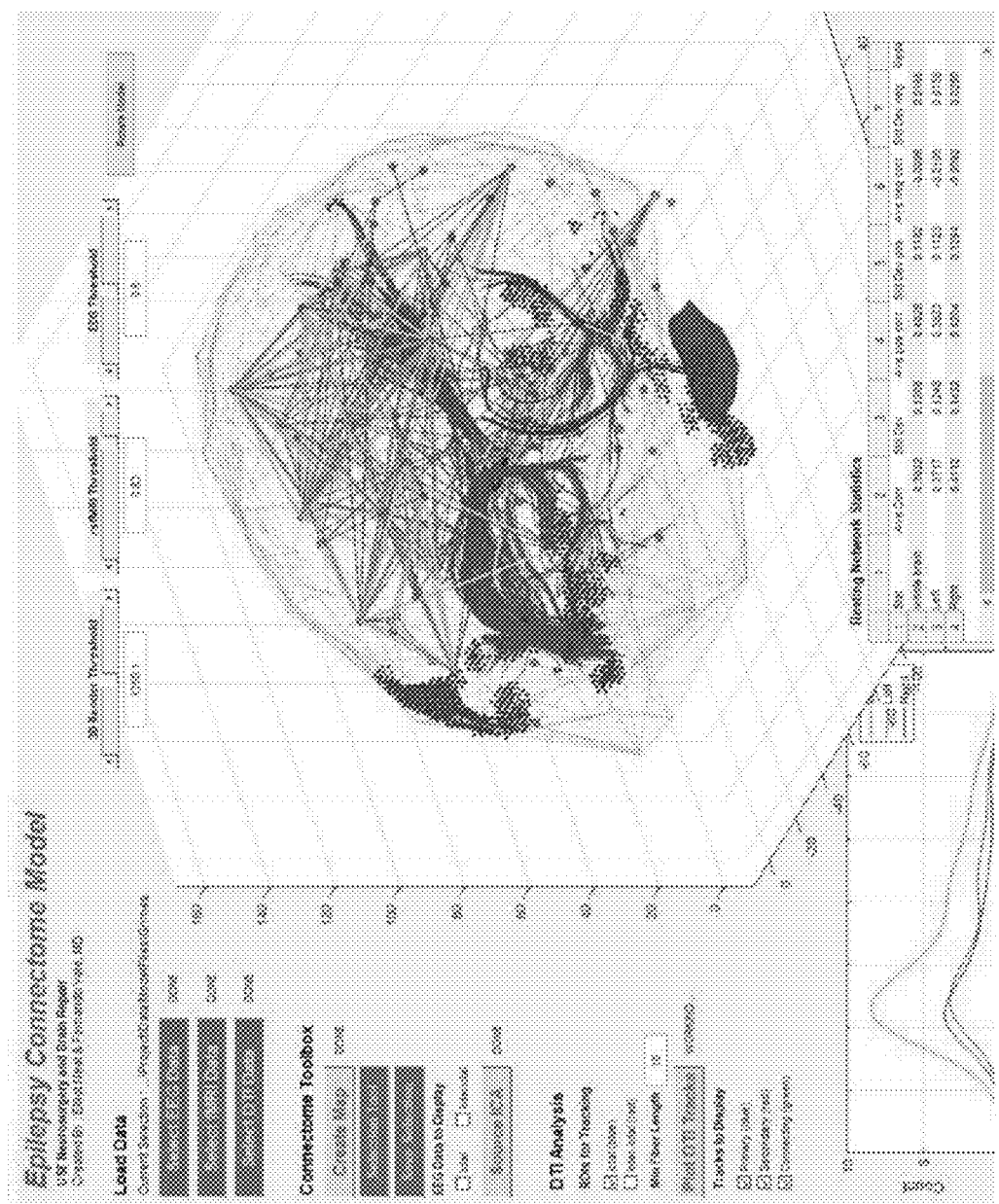
FIG. 5 depicts DTI-MRI, which is used to detect white matter fiber tracks connecting the interictal source to the connecting voxels, in accordance with an embodiment of the present invention. These fibers map the epilepsy network that consists of functionally correlated gray matter and the connecting white matter. This model shows the anatomical connections that may represent potential surgical targets.

With reference to FIG. 4, to analyze fiber connections in the network mapping, a method 400 may include, after the 3D mapping of the patient's brain network has been generated 405, combining a diffusion tensor MRI (DT-MRI) mapping to create a 3D network map of each patient. The method 400 may include, importing a diffusion tensor MRI volume into a tractography pre-processor 410. The method further includes interpolating the DT-MRI data and calculating a diffusion tensor for each voxel of the DTI-MRI data 415. The tractography pre-processor may then be used for calculating all fibers above a certain fractional anisotropy threshold 420, as may be defined by the user. Next, the fibers that cross through ROIs selected by the user are shown on the 3D map 425. For example, fibers connecting the interictal source location and the resting state correlation voxels would be shown, to visualize the theoretical interictal seizure network, as shown in FIG. 5.

In an additional exemplary embodiment, three illustrative sample cases are presented. In the healthy control case, the software showed symmetrical global connectivity. In the right temporal lobe epilepsy case, asymmetry was found in the global connectivity metrics with a paucity of connectivity ipsilateral to the epileptogenic cortex. The superior longitudinal fasciculus, uncinate fasciculus, and commissural fibers connecting disparate and discontinuous cortical regions involved in the epilepsy network were visualized. In the case with bitemporal lobe epilepsy, global connectivity was symmetric. It showed a network of correlating cortical activity local to epileptogenic tissue in both temporal lobes. The network involved white matter tracks in a similar pattern to those seen in the right temporal case.

In this exemplary embodiment, the method was applied in three illustrative sample cases. These cases were selected because they present with disparate preoperative diagnoses that most likely represent situations with variable neural network characteristics. The first sample case is a healthy control, the second patient is a typical case of mesial temporal lobe epilepsy (MTLE), and the last one is a patient with bitemporal seizure onset.

First, a 27-year-old male with no history of neurological disorders was analyzed as a healthy control. The second sample case was a 33-year-old female patient with left temporal lobe epilepsy with an eight-year history of intractable epilepsy. Long-term EEG monitoring (LTM) revealed slow, sharply contoured rhythmic 1- to 2-Hz delta activity evolving to spike-wave and polyspike-wave 2-Hz morphology, which disseminated to the left frontocentral and contralateral temporal regions and generalizes within 3 s. Wada testing showed that expressive language lateralized to the right hemisphere and that memory was supported primarily in the right hemisphere. Positronemission tomography showed mild left mesial temporal hypometabolism. The third sample case was a 25-year-old male patient with bitemporal seizure onset with a history of seizures for five years. Long-term EEG monitoring showed frequent interictal sharp waves in the right temporal region and rare, less well-formed sharp waves in the left temporal region. Seven of eight seizures had left hemispheric onset with a burst of rhythmic 7- to 8-Hz theta/alpha activity over the left frontotemporal region with evolution to rhythmic 3- to 4-Hz delta/theta activity and at times followed by periodic sharp waves at 0.5-1 Hz lasting 30-90 s. The only seizure with a right-sided onset showed a burst of rhythmic 11- to 12-Hz alpha activity in the right frontotemporal region with evolution to rhythmic 3- to 4-Hz theta/delta activity and followed by periodic sharp waves at 0.5 Hz lasting 90 s. Wada testing showed that language expression and memory were supported bilaterally.

Electroencephalography and rsfMRI were obtained as part of a standard epilepsy workup. Electroencephalography was acquired with twenty-four scalp electrodes in a standard International 10-20 configuration using an off-the-shelf Natus Neurology Long-Term-Monitoring EEG system (Natus Medical Inc., Pleasanton, Calif.). Resting state functional MRI was conducted in a 3-Tesla MRI scanner (Siemens, Munich, Germany) with a blood oxygenation level-dependent (BOLD) MRI sequence. Resting state functional MRI was acquired for a single run of 5 min with a repetition time (TR) of 3000 ms with the patient lying supine with eyes closed. Axial, noncontrast T1-weighted MRI with 1-mm slice thickness was acquired for accurate and precise co-registration with MNI brain models. Diffusion tensor MRI (DTI-MRI) was acquired to map white matter pathways. All MRI sequences were acquired in one single session, and the patient's head was stabilized to avoid any movement between scans so that the images would be preregistered.

Magnetic resonance imaging and EEG preprocessing steps were performed using SPM12 (Wellcome Department of Imaging Neuroscience, University College London. UK). Electroencephalography data were cropped to include representative ictal and interictal waveforms (MATLAB 2016b, Natick, Mass.). For the right temporal sample case, one ictal event 10 s in duration at a 256-Hz acquisition rate was analyzed. For the bitemporal case, 5 ictal events were analyzed lasting 8, 8, 22, 30, and 38 s. Electroencephalography data were band-pass filtered between 0.1 and 100 Hz to remove non-physiologic signals and notch filtered between 59 and 61 Hz to remove background electronic noise. T1-weighted MRI was transformed into Montreal Neurological Institute (MNI) space using the six-parameter rigid body spatial transformation algorithm built into the SPM12 fMRI toolbox. Twenty-four scalp electrodes in the standardized 24-electrode International 10-20 configuration were co-registered with a patient-specific brain mesh model generated from the thin-slice T1 MRI sequence using the SPM12 EEG source localization toolbox. The mesh was generated using a transformed canonical mesh in MNI space in SPM12 using the surface matching algorithm generated from a tessellated skin surface thresholded from the thin-slice T1 MRI. Forward computation for every cortical dipole was followed by an empirical Bayesian approach to inverse reconstruction to localize the evoked response. This set of 3-dimensional source-localization data in MNI space was exported as a volume and co-registered to the functional BOLD images by applying the same linear transformation that was calculated for the thin-slice T1 MRI in earlier steps to the rsfMRI dataset. Resting state functional MRI and T1 MRI were acquired consecutively; therefore, accurate co-registration could be assured of the rsfMRI and T1 MRI based on the assumption that there was no significant movement of the patient's head between the two MRI image sets. Then, the user selects all or a subset of the EEG source localization locations to generate a volume used for subsequent network mapping.

In accordance with the method of the present invention, predetermined regions of interest (ROI) volumes in MNI space were used from a study that isolated cortical co-activation patterns and converted the locations into groups of ROIs involved in resting state neural networks. For each ROI, inclusive voxels' time series functions were used collectively to generate median time series data scaled to the mean. Pearson linear correlation coefficient for each ROI-to-ROI connection was calculated and used to generate correlation scalars. These were converted into MNI space to construct a 3D graph with mapped vectors representing pairs of correlating ROIs. A more targeted approach was taken to visualize the network connectivity relating specifically to the epileptogenic cortex. The time series function for the user-defined segment of interictal source volumes was extracted. Pearson coefficients were calculated for every intra-axial voxel and highly correlated regions were mapped in MNI space.

The DTI-MRI was acquired consecutively to the T1 MRI and rsfMRI, so the linear transformation generated by SPM12 was applied to co-register the DTI-MRI with rsfMRI and T1 MRI in MNI space. The DTI-MRI was interpolated, eddy currents were corrected, and the diffusion tensor was calculated for each voxel (Diffusion Toolkit, Department of Radiology, Massachusetts General Hospital). A deterministic fiber assignment by continuous tracking (FACT) tractography algorithm was used to graph white matter fasciculi. Fibers intersecting with the epilepsy network volumes were extracted and co-registered to the 3D model. Categorical variable frequencies were compared using the Wald method to compute 99% confidence interval. A two-sample t-test was used to compare independent groups with continuous variables. p-Values less than 0.05 were considered significant. All statistical tests were conducted using GraphPad Prism 7 (GraphPad Software Inc., San Diego, Calif., USA).

Figure 6:
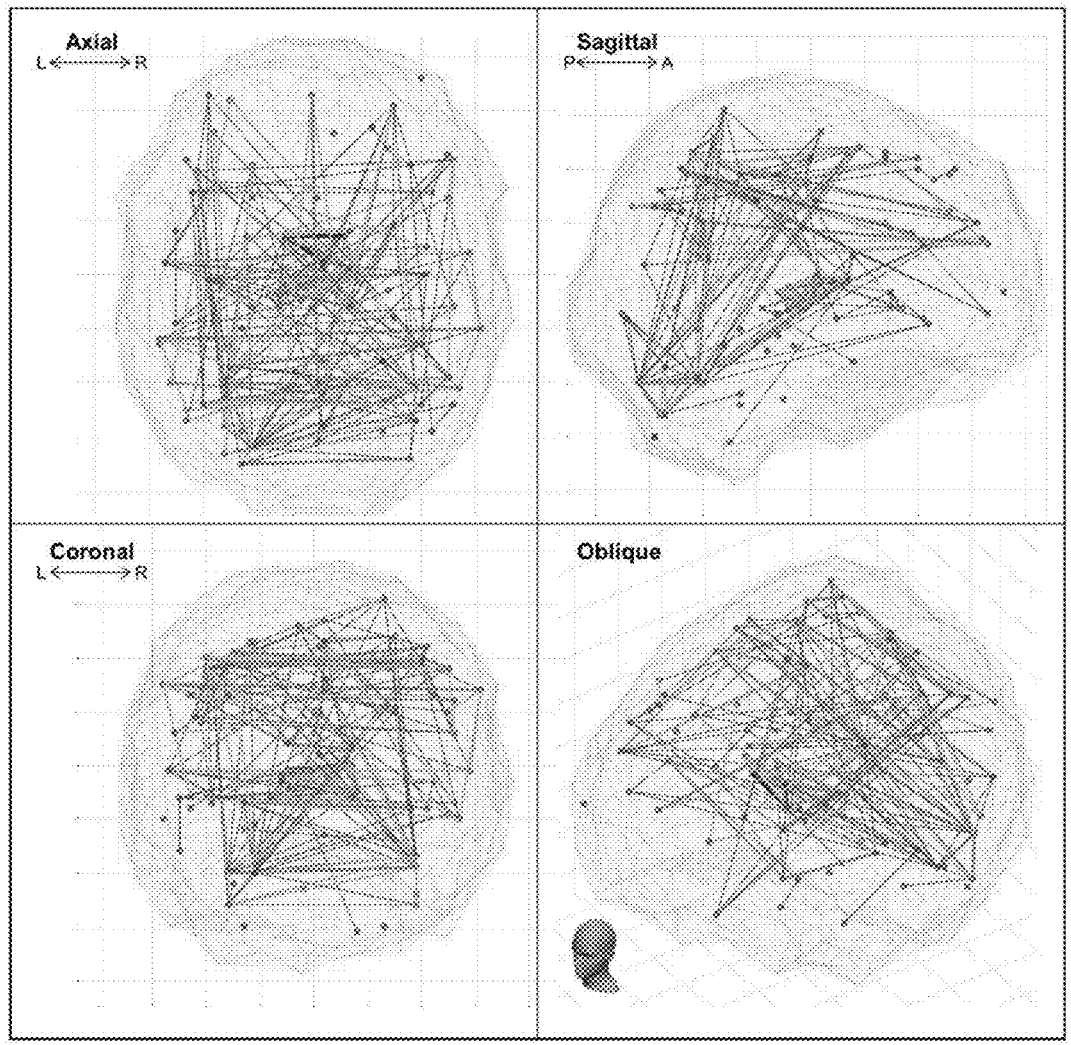
FIG. 6 illustrates the global resting network in a healthy control patient, in accordance with an embodiment of the present invention. The 3-dimensional model is displayed in three orthogonal planes and one oblique plane. Each blue dot represents a the centroid of a single functional ROI and lines connecting those dots represent a graph edge between the two corresponding ROIs. Connection lines are weighted by thickness and color indicative of Pearson correlation coefficient. Blue lines represent the connections with lowest Pearson coefficients, with green, orange and red representing increasing correlation. In the healthy patient, there is a qualitative symmetry of connections between the left and right hemispheres.

The resting network analysis method using predefined functional ROIs was tested on a healthy control subject without epilepsy. The global functional network was graphed with the edges color-coded to represent relative correlation strength quantified by a Pearson linear correlation coefficient, as shown in FIG. 6. Qualitatively, it was observed that functional networks segregated within subgroups determined empirically in a previous seminal resting fMRI study, as shown in FIG. 7A. It was confirmed that this resting network model captured a network that was grossly symmetric on inspection. This was quantified by measuring the frequency of graph edges with Pearson correlation coefficients above the global mean. With a confidence interval of 99%, edges were symmetrically distributed between left and right hemispheres, as shown in FIG. 7B. The ROIs were categorized by their degree of connections, which was defined as the number of connections that had an above-mean Pearson coefficient. It was found that degree of connection was not significantly different between left (41.2±16.7 connections) and right (43.7±16.7 connections) hemispheres (FIG. 2C).

The method of the present invention for the global model of the resting network was applied to an MRI of a patient with focal temporal lobe epilepsy. Qualitative analysis of the global resting network revealed clear asymmetry between left and right hemisphere connectivity. The left hemisphere exhibited a decreased number of edges with above-mean Pearson coefficients, as shown in FIG. 8A. This finding was supported with quantitative analysis; edges with above-mean Pearson coefficients were greater in number on the right side, contralateral to the epileptogenic zone, compared with the left side with a 99% confidence interval, as shown in FIG. 8B. It was found that ROI degree of connection was significantly (p b 0.01) higher in the right hemisphere (44.7±16.4 connections) compared with the left hemisphere (37.3±20.5 connections), as shown in FIG. 8C.

Figure 9A:
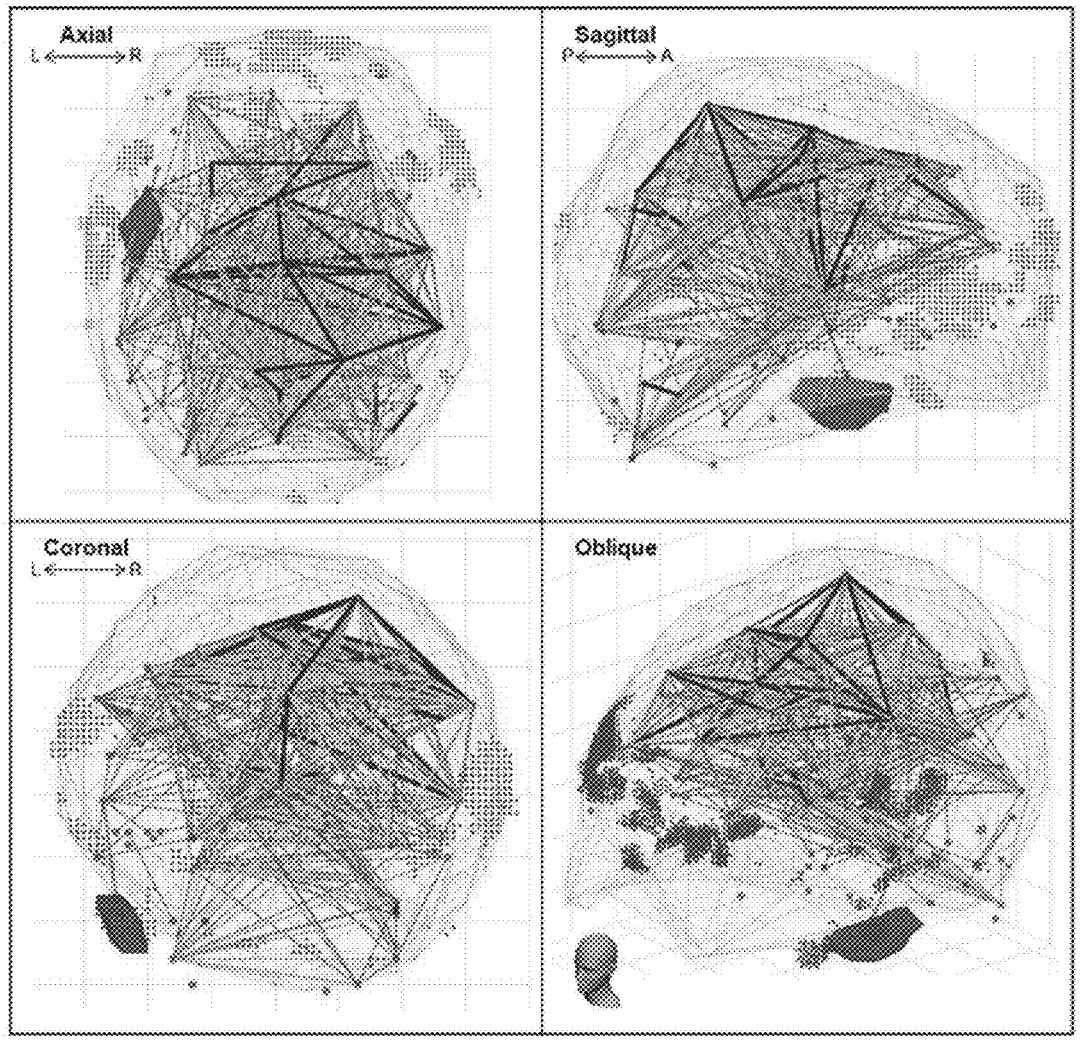
FIG. 9A illustrates the modeled epilepsy resting network for the unilateral case, where the map is now co-registered with the epileptogenic region (blue volume) and the co-activating brain regions (blue dot field). The co-activated brain regions are located bilaterally in the frontal, temporal, and occipital lobes and are discontinuous with the epileptogenic zone.

The ictal event that was selected for analysis was localized to the left temporal lobe, consistent with the neurologist's EEG assessment. The epilepsy network model showed the correlating cortical activity, suggestive of a connection to the epileptogenic cortex, in a 3D graph. Mapped correlating voxels were primarily grouped in distinct areas in both frontal lobes, both temporal lobes, and sparsely in the right occipital lobe, as shown in FIG. 9A. Interestingly, the neurologist's reading of this patient's EEG denoted ictal spread from the left temporal focus to a frontotemporal distribution.

Figure 9B:
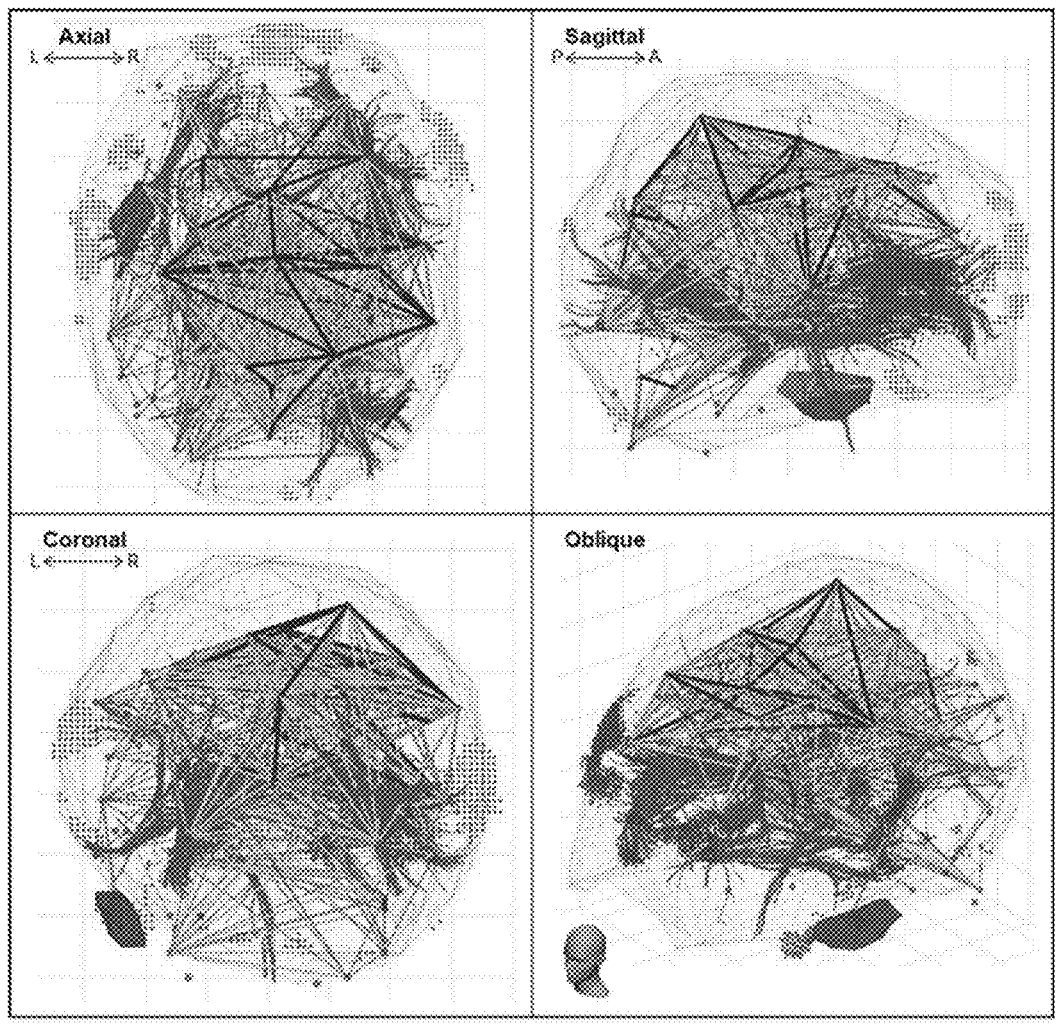
FIG. 9B illustrates the map for the patient with focal, left temporal lobe epilepsy, it is shown that the white matter pathways that intersect with the cortical regions that are activated in conjunction with the epileptogenic zone. Involved pathways are located bilaterally and involve the superior longitudinal fasciculus, uncinate fasciculus, and commissural fibers.

Diffusion tensor imaging tractography data were co-registered to display white matter pathways that may be involved with the mapped epilepsy network. Fibers intersecting the ictal source localization ROI were localized to the cortex within the temporal lobe. Fibers intersecting the rsfMRI correlating voxels show a much further reaching connection map. The uncinate fasciculus connecting both temporal lobes and their respective frontal lobes were identified as part of the network. Longitudinal fibers likely representing the inferior and superior longitudinal fasciculi were visualized bilaterally. Commissural fibers connecting the prefrontal cortex and passing through the genu of corpus callosum were also mapped. At the splenium of the corpus callosum, another fiber bundle was mapped that connects the left and right occipital lobes, as shown in FIG. 9B. Subsequently, this patient underwent mesial temporal lobectomy without preceding intracranial EEG recording. The surgical pathological specimen analysis found a severe hippocampal sclerosis pattern. Eight months after surgery, this patient remains seizure-free. So far, the seizure-free outcome suggests the successful disconnection and resection of the epileptogenic cortex, and therefore indicates that the preoperative mapping correctly localized to the epileptogenic zone.

Figure 10A:
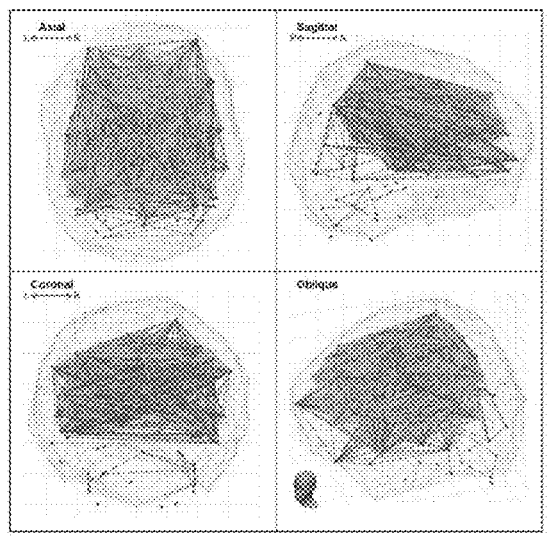
FIG. 10A illustrates the bitemporal lobe epilepsy, where the global network model shows a qualitative symmetry of edges in the left hemisphere compared with the right hemisphere.
Figures 10B, 10C:
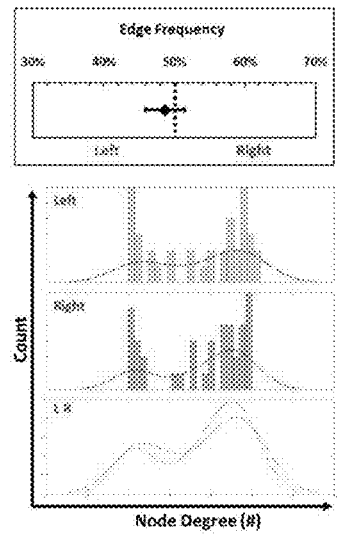
FIG. 10B illustrates the statistical analysis that reveals that frequency of edges with above-mean Pearson coefficients is not significantly asymmetrical (99% confidence interval).
FIG. 10C illustrates nodal connectivity in the left (34.6±22.9 connections) and right (35.6±21.4 connections) hemispheres was also not significantly asymmetrical (p=0.77).

Qualitative analysis of the global resting network revealed a grossly symmetrical global network. Edges with above-mean Pearson coefficients were symmetrically distributed between left and right hemispheres, as shown in FIG. 10A. This finding was supported with quantitative analysis; edges with above-mean Pearson coefficients were not significantly different between left and right hemispheres with a 99% confidence interval, as shown in FIG. 10B. It was found that ROI degree of connection was not significantly different (p=0.77) in the left hemisphere (34.6±22.9 connections) compared with the right hemisphere (35.6±21.4 connections), as shown in FIG. 10C.

Figure 11A:
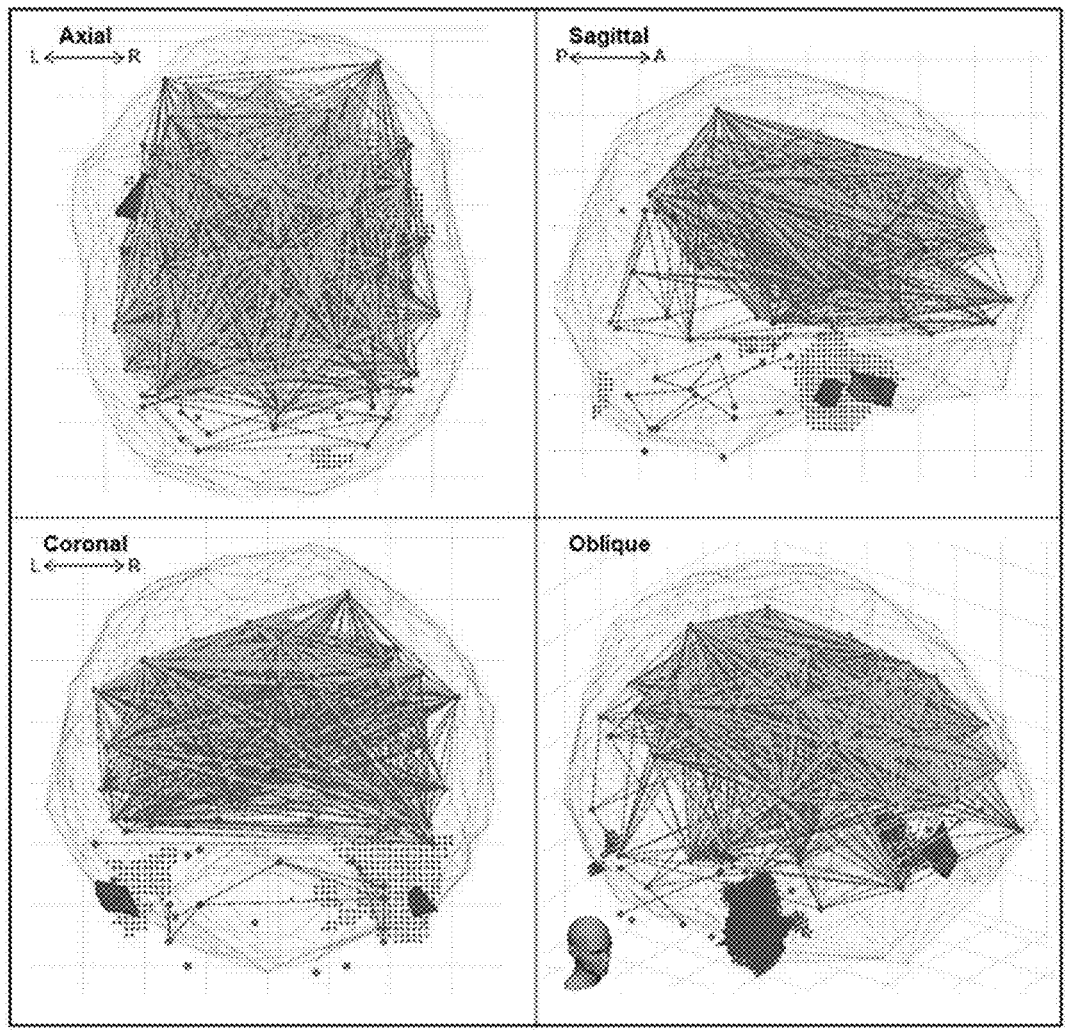
FIG. 11A illustrates the modeled epilepsy resting network for the bilateral case, where the epileptogenic cortex was localized to the left and right temporal lobes (blue volumes). Correlating cortical activity was found predominantly in the left and right temporal lobes as well, and it was continuous with the epileptogenic tissue.
Figure 11B:
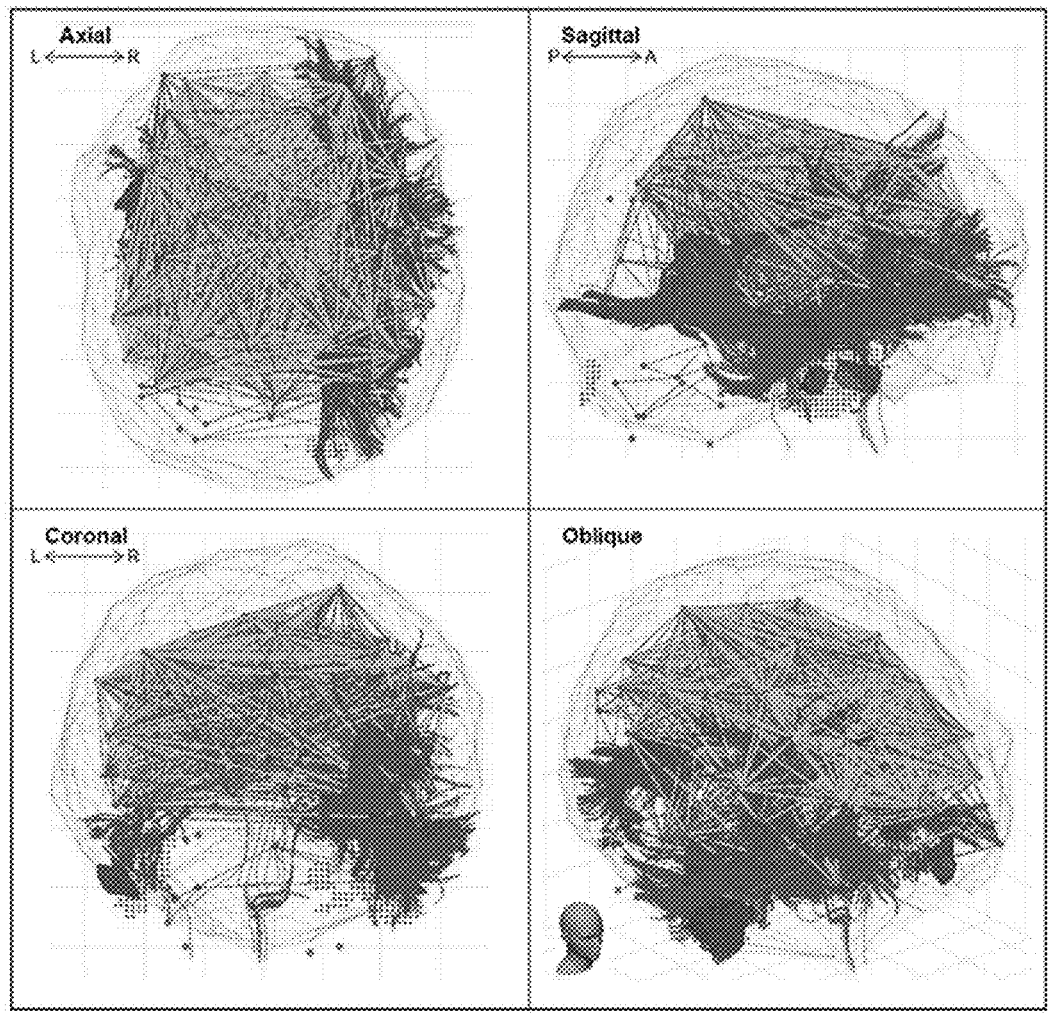
FIG. 11B illustrates involved white matter pathways are grossly similar in distribution to those in the case of right temporal lobe epilepsy, including the superior longitudinal fasciculus, uncinate fasciculus, and commissural fibers.

Electroencephalography source localization revealed that ictal discharges localized to the left and right temporal lobes. Cortical locations correlating with epileptogenic tissue were grouped in the left and right temporal lobes, continuous with the mapped seizure onset, as shown in FIG. 11A. Unlike the unilateral case, the network map in this patient did not show a widespread co-activating cortex discontinuous with the epileptogenic zone. Diffusion tensor imaging tractography analysis showed fibers intersecting with the putative epilepsy network in a similar pattern to the right temporal case. The uncinate fasciculus connecting both temporal lobes and longitudinal fibers likely representing the inferior and superior longitudinal fasciculi was visualized bilaterally. Commissural fibers connecting the left and right frontal cortex and passing through the corpus callosum were also mapped, as shown in FIG. 11B. Subsequent evaluation of this patient included bilateral placement of both surface and depth electrodes for intracranial EEG recording. Consistent with the results from the modeling method, intracranial recordings suggested a bitemporal seizure onset, and the patient was consequently implanted with a responsive neurostimulation (RNS) device (NeuroPace Inc., Mountain View, Calif.) to control seizures with evident bitemporal onset. Three months of electrocorticography (ECoG) measured by the RNS device also revealed bilateral seizure onset.

The present invention provides a novel technique for visualizing brain networks related to epileptogenic tissue and for modelling networks in a healthy patient and a putative epilepsy network in two patients with temporal lobe epilepsy. Unlike preexisting technologies that map the epilepsy network, this method is the first to use only nonconcurrent and noninvasive techniques.

This present invention leverages multimodal data including EEG, rsfMRI, and DTI-MRI. Presurgical evaluation of patients with epilepsy using multimodal diagnostic techniques is a necessary tool for a successful postoperative outcome. Intracranial recordings, using invasive electrodes, have been regarded as the gold standard for the identification of seizure-onset zones. However, invasive electrode placement has limited spatial coverage, and it is not without risks. Thus, a noninvasive method that can reliably model epileptic networks and localize the epileptogenic zone is highly desirable. Here, is presented a new method to evaluate epileptic networks based on commercially available hardware and the preliminary data gathered through it. These data show the potential role of this network-modeling software in pre-surgical evaluation as it resolved differences in network connectivity between cases with disparate diagnoses, and those connectivity measures were consistent with pre-surgical evaluations conducted using traditional techniques.

The modeling method of the present invention allows better definition of the global brain network and potentially demonstrates differences in connectivity between an epileptic and a non-epileptic brain. This finding may be useful for mapping cortico-cortical connections representing the putative epilepsy networks. With this methodology, the epileptogenic brain is localized and showed network asymmetry and long-distance cortical co-activation. This method is the first to use a multimodal, nonconcurrent, and noninvasive approach to model and visualize the epilepsy network. Multimodal techniques are more desirable than analysis of a single data type because it becomes possible to pick and choose the benefits of each individual technology while masking or reducing the noise and limitations of others. This noninvasive, multimodal analysis algorithm has the potential to benefit any patient carrying a diagnosis of focal epilepsy, regardless of their candidacy for surgery.

The present invention may be embodied on various computing platforms that perform actions responsive to software-based instructions and most particularly on touch-screen portable devices. The following provides an antecedent basis for the information technology that may be utilized to enable the invention.

Figure 12:
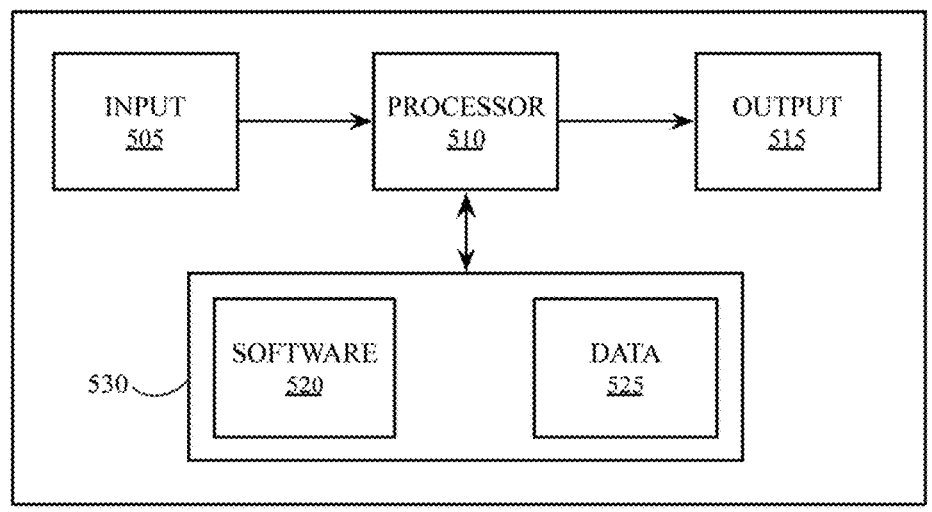
FIG. 12 is a block diagram illustrating a system for generating a 3D mapping of a patient's functional brain network, in accordance with an embodiment of the present invention.

FIG. 12 illustrates a block diagram of an example system 500 that can be used for producing functional brain mapping of a patient. The system 500 generally may include an input 505, at least one processor 510, a memory 530, an output 515 and any device for reading computer-readable media (not shown). The system 500 may take the form of a workstation, a notebook computer, a personal digital assistant (PDA), a multimedia device, a network server, a mainframe or any of a variety of other general-purpose or application specific computing devices. The system 500 may operate either automatically or semi-automatically or may read executable software instructions from a computer-readable medium, such as a hard drive, a CD-ROM, flash memory, etc., or may receive instructions from a user via a Graphical User Interface (GUI), or any other source logically coupled to a computer or device, such as a networked computer or server, via the input 505.

The input 505 may take on various forms, including the ability to provide for selecting, entering or otherwise specifying the parameters consistent with operating the system 500. For example, the input 505 may be designed to accept the EEG data and rsfMRI data of a patient. The input 505 may additionally be designed to accept user input, such as defining regions of interest of a patient's brain.

The at least one processor 510 of the system 500 may be configured to receive the data from the input 505 and may be further processed by the processor 505, in accordance with the software 520 stored in the memory 530. In some respects, the at least one processor 510 may be used to perform computations using digital and analog filters, time-series signal processing from time series rsfMRI data. The at least one processor 510 may be configured for cropping the EEG data to provide ictal and interictal characteristic waveforms, for band-pass filtering the cropped data, for notch filtering the cropped band-pass data, for inversely solving the cropped, band-pass filtered and notch filtered data to generate 3D spatial coordinates, for exporting the 3D spatial coordinates and the EEG data as a 3D volume and for overlaying the 3D volume on a 3D mesh from the rsfMRI data. The at least one processor 510 may further be configured to define ROIs for each ictal and interictal event from the EEG data, to extract median time series data from the rsfMRI data for each ictal and interictal event ROI, to compare the median time series for each ictal and interictal event ROI to each rsfMRI voxel time series to determine a correlation value for the voxel and to export 3D volumes of the voxels having correlation values exceeding a predetermined threshold. The at least one processor 510 may additionally be configured to define functional regions of ROIs from the rsfMRI data, to calculate and extract median MRI time series data for each ROI, to compare the time series data for each ROI to every other ROI time series data to calculate a correlation coefficient for each ROI-to-ROI connection and to generate correlation scalars and to construct a 3D graph with mapped vectors representing pairs of correlating ROIs based on the correlation scalars.

The memory 530 may include software 520 and data 525 and may be configured for storage and retrieval of processed information and data to be processed by the at least one processor 510. The software 530 may contain instructions directed to performing a process for generating a 3D functional mapping of a patient's brain network, as previously described. The data 525 may include any data necessary for operating the system 500 and may include any raw or processed information in relation to the EEG data or rsfMRI data.

The output 515 may take any form as necessary and may be configured for displaying, in addition to other desired information, any information related to the 3D mapping of the patient's brain network, the EEG data or the rsfMRI data.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for generating a 3D functional brain map of a patient, the method comprising:
   providing electroencephalogram (EEG) data acquired non-invasively from a patient during a first time period;
   cropping the EEG data to provide representative ictal and interictal events;
   identifying a set of regions of interest (ROIs) for each ictal and interictal event extracting median time series data from the set of ROIs for each ictal and interictal event;

providing resting state functional magnetic resonance imaging (rsfMRI) data acquired non-invasively from the patient during a second time period, wherein the first time period is different than the second time period, and wherein the rsfMRI data comprises a set of time-series rsfMRI voxels;

identifying a set of functional regions of interest (ROIs) for each rsfMRI voxel;

extracting median time series data from the functional ROIs of the rsfMRI data;

comparing the median time series for each ictal and interictal event ROI to each rsfMRI voxel time series to determine a correlation value for the voxel; and exporting 3D volumes of the voxels having correlation values exceeding a predetermined threshold to co-register the EEG data and the rsfMRI data of the patient to generate a 3D functional brain map of the patient illustrating a relationship between the ictal and interictal events of the patient and a resting state brain network of the patient.

2. The method of claim 1, further comprising:
band-pass filtering the cropped EEG data to remove nonphysiologic signals from the EEG data; and
notch filtering the band-pass filtered EEG data to remove background electronic noise from the EEG data.

3. The method of claim 2, further comprising:
inversely solving the cropped, band-pass filtered and notch filtered EEG data to generate 3D spatial coordinates that localize source of cortical discharges; and
exporting the 3D spatial coordinates from the EEG data as a 3D volume.

4. The method of claim 3, further comprising overlaying the 3D volume of a 3D mesh model from the rsfMRI data.

5. The method of claim 1, wherein
comparing the median time series for each ictal and interictal event ROI to each rsfMRI voxel time series to determine a correlation value for the voxel further comprises generating correlation scalars; and
constructing a 3D graph with mapped vectors representing pairs of correlating ROI's based on the correlation scalars.

6. The method of claim 1, further comprising:
performing tracing of the 3D functional brain map of the patient to identify a predicted surgical resection volume model; and
subtracting the 3D functional brain map of the patient that intersects with the predicted surgical resection volume model to generate a subtracted 3D functional brain map of the patient.

7. The method of claim 6, further comprising:
comparing the subtracted 3D functional brain map of the patient to the 3D functional brain map of the patient; and
assessing a predicted degree of disconnection based upon the comparison between the subtracted 3D functional brain map of the patient to the 3D functional brain map of the patient.

8. A system for non-invasively generating a 3D functional brain map of a patient, the system comprising:
an input for receiving electroencephalogram (EEG) data acquired non-invasively from a patient during a first time period and for receiving resting state functional magnetic resonance imaging (rsfMRI) data acquired non-invasively from the patient during a second time period, wherein the first time period is different than the second time period, and wherein the EEG data comprises ictal and interictal events and the rsfMRI data comprises a set of time-series rsfMRI data;

at least one processor and associated software for:
defining regions of interest (ROIs) for each ictal and interictal event;
extracting median time series data from the rsfMRI data for each ictal and interictal event ROI;
comparing the median time series for each ictal and interictal event ROI to each rsfMRI voxel time series to determine a correlation value for the voxel; and
exporting 3D volumes of the voxels having correlation values exceeding a predetermined threshold to co-register the EEG data and the rsfMRI data of the patient to generate a 3D functional brain map of the patient illustrating a relationship between the ictal and interictal events of the patient and a resting state brain network of the patient.

9. The system of claim 8, wherein the at least one processor and associated software are further configured for:
cropping the EEG data to provide representative ictal waveforms and interictal waveforms;
band-pass filtering the EEG data to remove nonphysiologic signals from the EEG data; and
notch filtering the band-pass filtered EEG data to remove background electronic noise from the EEG data.

10. The system of claim 9, wherein the at least one processor and associated software are further configured for:
inversely solving the cropped, band-pass filtered and notch filtered EEG data to generate 3D spatial coordinates that localize source of cortical discharges; and
exporting the 3D spatial coordinates from the EEG data as a 3D volume.

11. The system of claim 9, wherein the at least one processor and associated software are further configured for overlaying the 3D volume of a 3D mesh model from the rsfMRI data.

12. The system of claim 8, wherein the at least one processor and associated software are further configured for:
defining functional regions of interest (ROIs) from the rsfMRI data;
calculating and extracting median MRI time series data, scaled to the mean, for each ROI;
comparing the time series data for each ROI to every other ROI time series data to calculate a correlation coefficient for each ROI-to-ROI connection to generate correlation scalars; and
constructing a 3D graph with mapped vectors representing pairs of correlating ROI's based on the correlation scalars.

13. A non-transitory computer readable storage media having computer-executable instructions, having computer-executable instructions for performing a method of running a software program on a computing device for the generation of a 3D functional brain map of a patient, the computing device operating under an operating system, the method including issuing instructions from the software program comprising:
providing electroencephalogram (EEG) data acquired non-invasively from a patient during a first time period;
cropping the EEG data to provide representative ictal and interictal events;
identifying a set of regions of interest (ROIs) for each ictal and interictal event;
extracting median time series data from the set of ROIs for each ictal and interictal event;
providing resting state functional magnetic resonance imaging (rsfMRI) data acquired non-invasively from the patient during a second time period, wherein the first time period is different than the second time period, wherein the rsfMRI data comprises a set of time series rsfMRI voxels; and identifying a set of functional regions of interest (ROIs) for each rsfMRI voxel;

extracting median time series data from the functional ROIs of the rsfMRI data;

comparing the median time series for each ictal and interictal event ROI to each rsfMRI voxel time series to determine a correlation value for the voxel; and exporting 3D volumes of the voxels having correlation values exceeding a predetermined threshold to co-register the EEG data and the rsfMRI data of the patient to generate a 3D functional brain map of the patient illustrating a relationship between the ictal and interictal events of the patient and a resting state brain network of the patient.

14. The media of claim 13, further comprising:

band-pass filtering the cropped EEG data to remove nonphysiologic signals from the EEG data; and notch filtering the band-pass filtered EEG data to remove background electronic noise from the EEG data.

15. The media of claim 14, further comprising:

inversely solving the cropped, band-pass filtered and notch filtered EEG data to generate 3D spatial coordinates that localize source of cortical discharges; and exporting the 3D spatial coordinates from the EEG data as a 3D volume.

16. The media of claim 15, further comprising overlaying the 3D volume of a 3D mesh model from the rsfMRI data.

17. The media of claim 13, further comprising:

comparing the median time series for each ictal and interictal event ROI to each rsfMRI voxel time series to determine a correlation value for the voxel further comprises generating correlation scalars; and constructing a 3D graph with mapped vectors representing pairs of correlating ROI's based on the correlation scalars.

* * * * *